(12) United States Patent
Kim et al.

(10) Patent No.: US 8,895,765 B2
(45) Date of Patent: Nov. 25, 2014

(54) METHOD AND APPARATUS FOR PREPARING ALKYL ESTER FATTY ACID USING FATTY ACID

(75) Inventors: Soo-Hyun Kim, Incheon (KR); Hyun-Jun Cho, Seoul (KR); Chan-Woo Moon, Ulsan (KR); Byoung-Kyung Ham, Uiwang-si (KR); Jae-Bong Lim, Anyang-si (KR)

(73) Assignee: SK Chemicals Co., Ltd., Suwon-si (KR)

( * ) Notice: Subject to any disclaimer, the term of this patent is extended or adjusted under 35 U.S.C. 154(b) by 643 days.

(21) Appl. No.: 13/128,171

(22) PCT Filed: Sep. 22, 2009

(86) PCT No.: PCT/KR2009/005381
§ 371 (c)(1),
(2), (4) Date: May 6, 2011

(87) PCT Pub. No.: WO2010/053258
PCT Pub. Date: May 14, 2010

(65) Prior Publication Data
US 2011/0218355 A1    Sep. 8, 2011

(30) Foreign Application Priority Data

Nov. 7, 2008 (KR) .................. 10-2008-0110519

(51) Int. Cl.
| | |
|---|---|
| *C11C 3/04* | (2006.01) |
| *B01J 8/00* | (2006.01) |
| *C07C 67/08* | (2006.01) |
| *C11C 1/08* | (2006.01) |
| *C11C 3/00* | (2006.01) |
| *B01J 8/04* | (2006.01) |

(52) U.S. Cl.
CPC ............. *C07C 67/08* (2013.01); *B01J 8/0492* (2013.01); *C11C 1/08* (2013.01); *C11C 3/003* (2013.01); *Y02E 50/13* (2013.01)
USPC ........... 554/170; 554/124; 554/174; 422/607; 422/600; 422/610; 560/129

(58) Field of Classification Search
None
See application file for complete search history.

(56) References Cited

U.S. PATENT DOCUMENTS

| | | | |
|---|---|---|---|
| 4,164,506 A | 8/1979 | Kawahara et al. | |
| 4,608,202 A | 8/1986 | Lepper et al. | |

(Continued)

FOREIGN PATENT DOCUMENTS

| | | |
|---|---|---|
| DE | 2503195 A1 | 7/1976 |
| EP | 0 127 104 B1 | 12/1984 |

(Continued)

OTHER PUBLICATIONS

KR 10-2008-0041438, Cho, H. et al., Method for produing a fatty acid alkyl ester using fatty acid, English translation, 16 pages.*

*Primary Examiner* — Yate K Cutliff
(74) *Attorney, Agent, or Firm* — Birch, Stewart, Kolasch & Birch, LLP

(57) ABSTRACT

A method for preparing fatty acid alkyl ester for bio-diesel fuel is disclosed wherein fatty acid, specifically fatty acid distillate reacts with alcohol. The method does not require the glycerin purification process, and has the superior conversion ratio of fatty acid. The method for preparing fatty acid alkyl ester for bio-diesel fuel comprises the step of carrying out a counter current type esterification reaction of fatty acid and alcohol in each tray of a counter current column reactor at a temperature of 200 to 350° C. and a pressure of 1 to 35 bar. Here the raw material of the fatty acid is fed to an upper part of the counter current column reactor and the alcohol is fed to a lower part of the counter current column reactor. The counter current column reactor has a number of trays which are installed horizontally to have a number of vertical compartments. Each of the number of trays has an opening part at one end thereof to communicate one compartment with an adjoining compartment. The opening parts of two adjoining trays are alternately installed with each other.

8 Claims, 7 Drawing Sheets

(56) References Cited

U.S. PATENT DOCUMENTS

| | | | |
|---|---|---|---|
| 4,652,406 A | 3/1987 | Lepper et al. | |
| 5,040,941 A | 8/1991 | Wilding et al. | |
| 5,130,102 A * | 7/1992 | Jones, Jr. | 422/605 |
| 5,157,168 A | 10/1992 | Wilmott et al. | |
| 5,536,856 A * | 7/1996 | Harrison et al. | 554/164 |
| 5,844,111 A | 12/1998 | Granberg et al. | |
| 5,849,939 A | 12/1998 | Mittelbach et al. | |
| 5,945,529 A | 8/1999 | Corrigan et al. | |
| 2004/0151640 A1 | 8/2004 | Benfer et al. | |
| 2010/0228042 A1 | 9/2010 | Chun et al. | |
| 2011/0028747 A1 | 2/2011 | Cho et al. | |

FOREIGN PATENT DOCUMENTS

| | | |
|---|---|---|
| EP | 0 184 740 B1 | 6/1986 |
| EP | 0 708 813 B1 | 5/1996 |
| GB | 2109265 A | 6/1983 |
| JP | 42-17163 | 9/1967 |
| KR | 10-0151550 B1 | 5/1999 |
| KR | 2002-0029131 A | 4/2002 |
| KR | 10-2004-0087625 A | 10/2004 |
| KR | 10-2004-0101446 A | 12/2004 |
| KR | 10-2007-0106236 A | 11/2007 |
| KR | 10-2008-0041438 A | 5/2008 |
| WO | 90/08127 A1 | 7/1990 |
| WO | WO 96/40415 A1 | 12/1996 |
| WO | WO 02/087723 A1 | 11/2002 |
| WO | WO 03/087278 A1 | 10/2003 |
| WO | WO 2007/126166 A1 | 11/2007 |
| WO | WO 2009/123369 A1 | 10/2009 |

* cited by examiner (a) Stirred tank reactor      (b) Column reactor (a) Continuous stirred tank reactor (b) Column reactor

METHOD AND APPARATUS FOR PREPARING ALKYL ESTER FATTY ACID USING FATTY ACID

FIELD OF THE INVENTION

This invention relates to a method and an apparatus for preparing fatty acid alkyl ester using fatty acid, and more particularly to a method for preparing fatty acid alkyl ester for bio-diesel by reacting fatty acid, specifically fatty acid distillate with alcohol at high pressure. The method does not require the glycerine purification process, and has the superior conversion ratio of fatty acid.

BACKGROUNDS OF THE INVENTION

Diesel, among the various fuels derived from crude mineral oils, has some advantages such as good fuel efficiency, low cost and low carbon dioxide generation. On the other hand, there is a problem that the combustion of diesel produces a large quantity of air pollution. In order to solve these problems, various researches have been conducted on alternative fuel which has similar physical property to diesel, and is economically preferable, and also can prevent the air pollution. The bio-diesel has similar physical property to diesel oil, remarkably reduces air pollution, and is a naturally recycling energy source. Generally, the bio-diesel is produced by trans-esterification reaction of vegetable oil such as rapeseed oil, soybean oil, sunflower oil, palm oil, etc, animal fats, waste cooking oil, and so on with alcohol in the presence of acid catalyst or alkali catalyst. In the production of the bio-diesel, about 10 weight % of glycerin with respect to the total amount of bio-diesel is produced as a by-product. Recently, since the plant construction for bio-diesel is rapidly and world-widely progressed, an oversupply of glycerin is expected.

On the other hand, oils and fats generally contain free fatty acids, which exist in the mixed form with triglyceride of fatty acid. The free fatty acids are separated as a by-product in the refining process of oils and fats. Several methods for preparing fatty acid alkyl ester from the separated free fatty acids have been known. The methods for esterification of the free fatty acids are disclosed in European patent publication No. 127104A, European patent publication No. 184740A and U.S. Pat. No. 4,164,506, and so on. In these methods, the esterification reaction is carried out by heating the mixture of fatty acid and fatty acid triglyceride with methanol at about 65° C. in the presence of sulfuric acid or sulfonic acid catalyst. European patent publication No. 708813A discloses the method for increasing the yield of the fatty acid alkyl ester from oils and fats. In the method, the free fatty acid is separated from glycerin phase which is the product of transesterification reaction, and then the separated free fatty acid is esterified. In this method, the free fatty acid is obtained by the neutralization of glycerin phase, and the obtained free fatty acid is reacted for 2 hours at about 85° C. in the presence of strong sulfuric acid catalyst, which reduces the amount of fatty acid from 50% to 12%. In addition, a method for improving esterification reaction efficiency of fatty acid is disclosed (Korean patent unexamined-publication No. 2004-0101446, International Publication No. WO 2003/087278), which utilizes a mechanical apparatus or supersonic waves for causing dynamic turbulence in a reactor. In this method, the esterification is carried out by reacting the fatty acid or fatty acid contained in oils and fats with alcohol at a high pressure and a high temperature using sulfuric acid or ion exchange resin as catalyst. Further, Korean patent unexamined-publication No. 2004-87625 discloses a method for removing free fatty acid from waste cooking oil, using solid acid catalyst. The above mentioned methods commonly use an acid catalyst, such as sulfuric acid etc. If such an acid catalyst is not completely removed after the reaction, the quality of bio-diesel is deteriorated. Therefore, complicate processes for neutralizing, filtering, washing and cleaning the acid catalyst must be needed, and there is the defect of high cost for production facilities because the reactors have a quality of corrosion resistance to acid such as sulfuric acid. Also, the life cycle of the solid acid catalyst such as ion exchange resin is not long and cost for recycling the same is expensive. Furthermore, in the above mentioned conventional methods, since the esterification of fatty acid is carried out at low temperature, water produced during the reaction is not efficiently removed to outside of the reaction system. Thus, the conversion ratio of fatty acid into fatty acid alkyl ester is low, and the physical properties of the obtained fatty acid alkyl ester are not suitable for bio-diesel.

Moreover, Korean patent unexamined-publication No. 2007-106136 and International applicaiton publication No. WO 2007/126166 which are owned by the present applicant, disclose a method and an apparatus for solving the above mentioned defects to some extent, but the method has a disadvantage of relatively slow rate of reaction for the absence of catalyst. And Korean patent unexamined-publication No. 2008-41438 and International application No. PCT/KR2008/1831 owned by the present applicant disclose a method which improves reaction rate and conversion ratio by using metal catalysts, but the method has a disadvantage of low efficiency of reaction because the removal of water produced during the esterification reaction is difficult when the reaction between fatty acid and alcohol is carried out at over 10 bar using the reactor disclosed in the above references. Moreover, when an esterification reactor which is conventionally designed for reactions at high pressure, for example, a conventional esterification reactor operated at high pressure of over 10 bar commercially, is used in the esterification reaction between fatty acid and alcohol, the removal of water produced during the reaction is not effective and it is difficult to manufacture fatty acid alkyl ester for bio-diesel of car fuel which demands high quality. Moreover, if the esterification reactor designed for reactions at high pressure is used at low pressure (under 10 bar) without additional modification of the reactor, the pressure of the reactor drops rapidly because the size of gas pipes, nozzles and heat exchangers around the reactor are relatively small, and the output should be reduced than the design capacity. On the contrary, to use the conventionally structured esterification reactor which is designed for reactions at high pressure without output reduction at low pressure, pipe lines, nozzles, heat exchangers around the reactor should be converted or replaced with a high cost.

SUMMARY OF THE INVENTION

Therefore, it is an object of the present invention to provide a method for economically preparing fatty acid alkyl ester suitable for bio-diesel fuel.

It is another object of the present invention to provide a method and an apparatus for efficient esterification reaction of fatty acid and alcohol even at high pressure, without catalyst or with metal catalyst.

It is still another object of the present invention to provide a method and an apparatus for preparing fatty acid alkyl ester, which are capable of using an esterification reactor operated at high pressure without any conversion.

In order to achieve these objects, the present invention provides a method for preparing fatty acid alkyl ester for bio-diesel fuel, which comprises the step of carrying out a counter current type esterification reaction of fatty acid and alcohol in each tray of a counter current column reactor at a temperature of 200 to 350° C. and a pressure of 1 to 35 bar. Here the raw material of the fatty acid is fed to an upper part of the counter current column reactor and the alcohol is fed to a lower part of the counter current column reactor. The counter current column reactor has a number of trays which are installed horizontally to have a number of vertical compartments. Each of the number of trays has an opening part at one end thereof to communicate one compartment with an adjoining compartment. The opening parts of two adjoining trays are alternately installed with each other.

Moreover, the present invention provides an apparatus for preparing fatty acid alkyl ester for bio-diesel fuel, which comprises a columnar reactor body; and a number of trays which are installed horizontally to have a number of vertical compartments in the reactor body and have gas valves in regular intervals. Wherein each of the number of trays has an opening part at one end thereof to communicate one compartment with adjoining compartment; the opening parts of two adjoining trays are alternately installed with each other; and a raw material of fatty acid is fed to an upper part of the columnar reactor body and alcohol is fed to a lower part of the columnar reactor body to carry out counter current type esterification reaction in each tray of the columnar reactor at temperature of 200 to 350° C. and pressure of 1 to 35 bar.

As stated above, the method and apparatus for preparing fatty acid alkyl ester according to the present invention can be used to prepare high quality fatty acid alkyl ester for bio-diesel by esterification reaction of fatty acid and alcohol at high temperature and low or high pressure (1 to 35 bar), without catalyst or with metal catalyst, unlike any conventional methods. Moreover, the method of the present invention does not require some processes such as neutralization, filtration and rinsing for removing acid catalyst, and fatty acid alkyl ester with high purity and conversion rate can be obtained simply with only two steps of distillation. Therefore, the whole process is simplified, and the costs for process equipments and operation can be reduced. Moreover, the method has the advantage of minimizing the alcohol use by collecting and reusing excess alcohol which does not participate in esterification reaction. Meanwhile, recently, many of the esterification reactors for preparing dimethyltetephtalate (DMT) which are operated at low or high pressure, have been shut down due to the reduced demand for DMT all over the world. The idle equipments such as the esterification reactors for preparing DMT are applicable to the method of the present invention with a minimum cost for equipment modification. The method of the present invention can be economically applicable to a small scale reactor, and also can be ideally applicable to a commercial scale reactor operated at wide pressure range. The produced fatty acid alkyl ester can be directly used as bio-diesel without any extra additional process.

DETAILED DESCRIPTION OF THE INVENTION

A more complete appreciation of the invention, and many of the attendant advantages thereof, will be better appreciated with reference to the following detailed description and the accompanying drawings.

Figure 1:
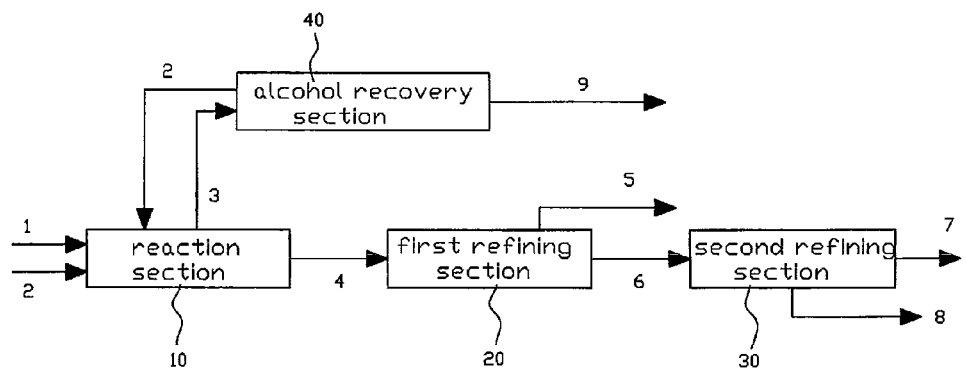
FIG. 1 is a drawing for showing an entire configuration of an apparatus for preparing fatty acid alkyl ester according to an embodiment of the present invention.

FIG. 1 shows an entire configuration of an apparatus which can be used for a method for preparing fatty acid alkyl ester according to an embodiment of the present invention. As shown in FIG. 1, fatty acid raw material 1 (hereinafter, if necessary, simply "fatty acid") and alcohol 2 are introduced into a reaction section 10 and then esterification reaction is carried out at a predetermined temperature and pressure. The crude fatty acid alkyl ester 4 produced at the esterification reaction is transferred to a first refining section 20, and the impurities 5 having low boiling point can be removed through the top of the distillation column of the first refining section 20 by distillation. The first refined fatty acid alkyl ester 6 is transferred to a second refining section 30, and distilled to leave residues and residual impurities 8 such as metal catalyst used in the reaction in the second refining section 30. The distilled and purified fatty acid alkyl ester 7 is discharged through the top of the distillation column of the second refining section 30. On the other hand, the reaction section 10 is connected to an alcohol recovery section 40 so that a mixture (alcohol/water 3) of water produced at the reaction section 10 and excess alcohol which is unreacted at the reaction section 10, is introduced into the alcohol recovery section 40. In the alcohol recovery section 40, the alcohol 2 is distillated and recycled to the reaction section 10 and water 9 is transferred to a waste water disposal plant.

In the present invention, as the fatty acid raw material 1 for preparing fatty acid alkyl ester 7, pure fatty acid (RCOOH) in which carbon atom number of aliphatic part (R) is 14 to 24, can be used. However, it is preferable to use fatty acid distillate as the raw material. The fatty acid distillate is produced as a by-product during the process of refining crude vegetable oil collected from vegetables such as rapeseed, soybean, sunflower, palm, or so on. The refining process can be carried out by a high pressure steam to obtain refined vegetable oil, such as rapeseed oil, soybean oil, sunflower oil or palm oil, or so on. If necessary, a mixture of the pure fatty acid and the fatty acid distillate can be used as the fatty acid raw material 1. The fatty acid distillate generally contains 65 to 95 weight %, preferably 80 to 85 weight % of the fatty acid in which carbon atom number of aliphatic part (R) is 14 to 24. The remaining components of the fatty acid distillate include β-carotin, fatty acid in which carbon atom number of aliphatic part (R) is less than 14 or more than 24, and so on. In the method for preparing fatty acid alkyl ester according to the present invention, it is economically advantageous to use the fatty acid distillate as the raw material. As the alcohol for the present invention, monovalent alcohols having 1 to 10 carbon atoms, preferably monovalent alcohols having 1 to 4 of carbon atom such as methanol, ethanol, propanol, or so on, and more preferably methanol, can be used.

The method for preparing fatty acid alkyl ester according to the present invention can be carried out without catalyst or with metal catalyst. When the method is carried out with metal catalyst, compounds containing metal element selected from the group consisting of cobalt, iron, manganese, zinc, titanium, antimony, germanium, zirconium, lead, and mixtures thereof can be used as the metal catalyst. Preferably acetates, oxides, alkoxides, hydroxides, carbonates and so on of the above mentioned metals, for example, cobalt acetate, manganese acetate, zinc acetate, iron acetate, germanium dioxide, tetrabutyl titanate, and so on can be used as the metal catalyst. It is preferable for the metal catalyst to be added to the esterification reaction as the form of alcohol solution. And it is preferable for the amount of metal element in the catalyst to be 30 to 200 ppm (by weight), more preferably 50 to 100 ppm to the fatty acid raw material. If the amount of the metal catalyst is less than the above mentioned range, it is economically undesirable because of the low reaction rate. And if the amount of metal catalyst is more than the above mentioned range, the reaction rate would not further increase, but it is only economically unfavorable. Meanwhile, if the fatty acid raw material contains impurities such as phosphorus (P) which inhibit the activity of the metal catalyst, it is desirable to increase the amount of the metal catalyst in responsive to the amount of the impurities. Moreover, in case of adding the metal catalyst to a reactor as alcohol solution, the amount of alcohol should be enough to completely dissolve the metal catalyst.

Figure 2:
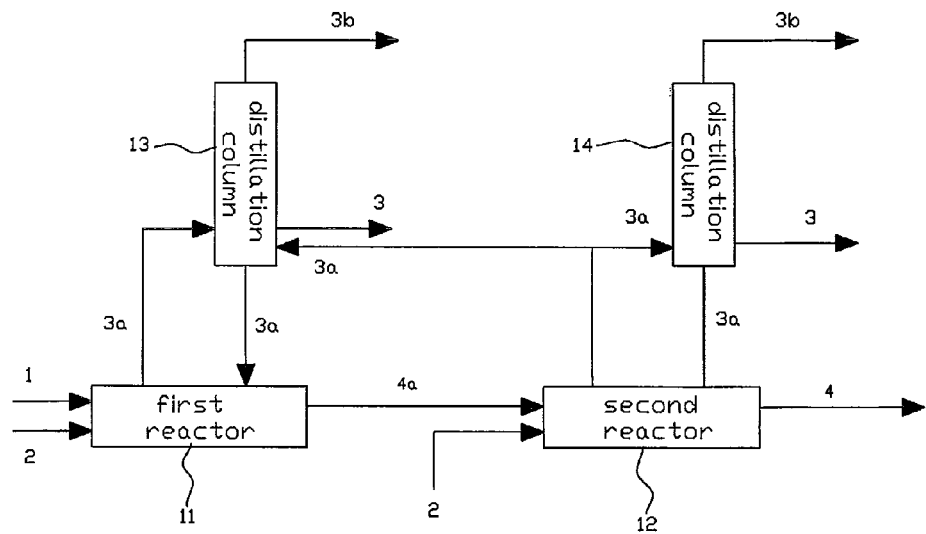
FIG. 2 is a drawing for showing an embodiment of the reaction section depicted in FIG. 1.

In the present invention, the esterification reaction can be carried out in one-step or two-step. In the one-step esterification reaction, the reaction section 10 is constituted by one reactor and one distillation column. In the two-step esterification reaction, the reaction section 10 may be constituted by two reactors and one distillation column where the one distillation column is commonly used, or one reactor and one distillation column can be used for each step as shown in FIG. 2. Moreover, the reactor and the distillation column may not be separated, but can be integrated, wherein the lower part of the integrated apparatus works as the reactor, and the upper part of the integrated apparatus works as the distillation column. In this case, a seal tray can be installed between the upper part for the distillation column and the lower part for the reactor to prevent water from falling from the upper part to the lower part. The esterification reaction according to the present invention is carried out by a continuous process, and can be carried out by one-step or divided two-step as previously described. The one-step reaction can provide a sufficiently high conversion ratio if the length of a stay is sufficient, however it is preferable to carry out the two-step reaction.

FIG. 2 shows an embodiment of the reaction section 10 in FIG. 1, which is constituted by two reactors 11, 12 and two distillation columns 13, 14. Referring to FIG. 2, a product 4a which is obtained by the reaction in the first reactor 11 is introduced into the second reactor 12 together with alcohol 2 for a second reaction in the second reactor 12. The crude fatty acid alkyl ester 4 which is the product of the second reaction in the second reactor 12 is transferred to the refining sections 20 in FIG. 1. The mixtures 3a containing water produced at each reactor 11, 12 and the excess alcohol which is unreacted are exhausted into the distillation columns 13, 14, respectively. The mixture 3a is separated in the distillation columns 13, 14 so that pure alcohol or the azeotrope of alcohol/water 3b is exhausted via the upper part of the distillation columns 13, 14 and the mixture 3 containing alcohol and water, in which the concentration of water is high, is exhausted through the lower part of the distillation columns 13, 14. Here, the pure alcohol or the azeotrope of alcohol/water 3b obtained at the upper part of the distillation columns 13, 14 can be reused as an alcohol which is introduced into the reaction section 10. The alcohol/water mixture 3, in which the concentration of water is high, is transferred to the alcohol recovery section 40 of FIG. 1.

Figure 3:
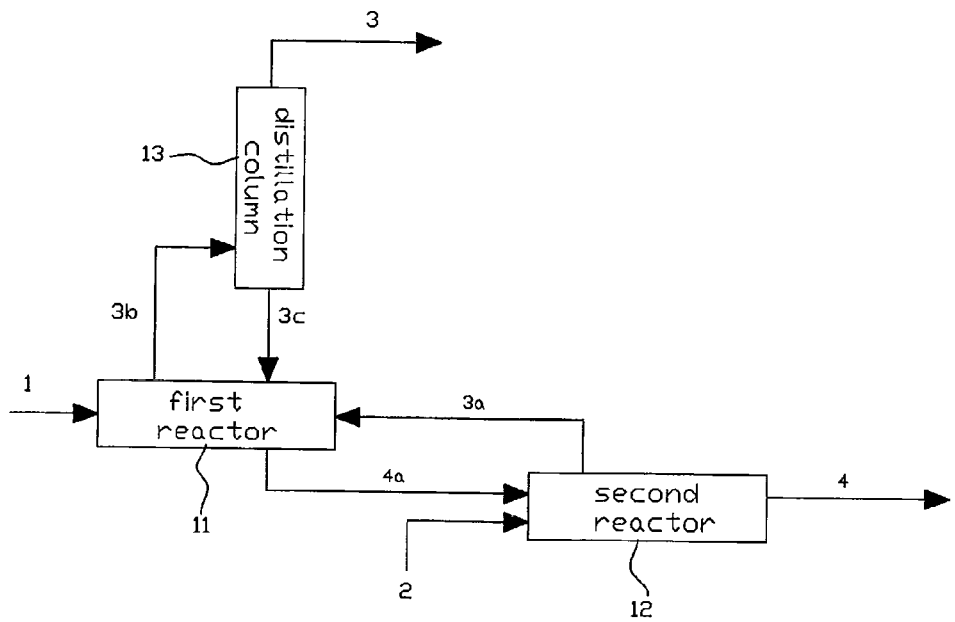
FIG. 3 is a drawing for showing another embodiment of the reaction section depicted in FIG. 1.

FIG. 3 shows another embodiment of the reaction section 10 in FIG. 1, which is constituted by two reactors 11, 12 and one distillation column 13. As shown in FIG. 3, the product 4a from the reaction somewhat carried out in the first reactor 11 is fed into the second reactor 12 with alcohol 2 for the second reaction, and the product from the second reaction, the crude fatty acid alkyl ester 4, is transferred to the refining sections 20, 30 in FIG. 1. The mixture 3a of water produced in the second reactor 12 and unreacted excess alcohol is fed into the first reactor 11 to participate in the first reaction. The mixture 3b of water generated from the first reactor 11, unreacted excess alcohol, and a little fatty acid alkyl ester is separated in the distillation column 13, so that alcohol/water mixture 3 from the upper part of the distillation column 13 is discharged to outside of the reaction section 10, and fatty acid alkyl ester/alcohol/water mixture 3c from the lower part of the distillation column 13 is fed into the first reactor 11 to prevent the loss of fatty acid alkyl ester. Here, alcohol/water mixture 3 from the upper part of the distillation column 13, whose water concentration is high, is transferred to the alcohol recovery section 40 of FIG. 1.

Hereinafter, the preparation conditions of fatty acid alkyl ester according to the present invention will be described in detail. The esterification reaction of the present invention is carried out at high temperature. Thus, high reaction rate and conversion ratio of fatty acid into fatty acid alkyl ester can be obtained in the present invention. The temperature for the esterification reaction is 200 to 350° C., preferably 250 to 320° C. The pressure for the esterification reaction is conventionally 1 to 35 bar, however, the method according to the present invention has characteristics showing high reaction rate and conversion ratio even at the high pressure of 10 to 35 bar, particularly 20 to 30 bar. If the reaction temperature and pressure are out of the above mentioned ranges, water produced by the esterification reaction between fatty acid and alcohol cannot be efficiently removed, the reaction rate and the conversion ratio of fatty acid may be reduced, or reverse reactions may occur. A conventional esterification reactor, especially an esterification reactor for preparing DMT(dimethylterephtalate) is designed to be operated at high pressure over 10 bar, and particularly in the conventional esterification reactor, pipes, heat exchangers and nozzles which are related to gas flow path are designed smaller than those of a reactor for reactions at low pressure. Therefore, if the esterification reactor is operated at low pressure, pressure loss is occurred, and an input of alcohol should be reduced followed by decreasing productivity. On the contrary, to maintain the design capacity of the esterification reactor at low pressure, pipe lines, nozzles and heat exchangers around the reactor should be converted to be the size suitable for low pressure condition, so that it costs a great deal.

However, if the reaction is carried out continuously in a counter current column reactor which has a number of trays, even at low and high pressure of 1 to over 35 bar, the reaction can be carried out at the same efficiency as the case of low pressure of 1 to 10 bar. When the esterification reaction of fatty acid and alcohol is carried out in the column reactor, the condition of counter current is satisfied by feeding fatty acid to the upper part of the reactor and alcohol to the lower part of the reactor to raise the efficiency of the reaction. Alcohol/water mixture discharged after the reaction with fatty acid in each tray is introduced only to the upper tray not to the lower tray because of high reaction temperature. Therefore, in the esterification reaction, there is little water and plenty of pure alcohol (for example, methanol) in the lower tray of the column reactor so that the condition for decreasing a reverse reaction can be made. Moreover, each tray guarantees enough stay-length of unreacted fatty acid by preventing the short pass of the unreacted fatty acid, and has the first-in first-out effect to raise the conversion efficiency. These advantages can make the optimum condition of the reaction for preparing fatty acid methyl ester of low acid value.

According to the present invention, when the continuous counter current column reactor is used for esterification reaction, all steps of reaction process can be carried out at pressure of 1 to 35 bar, preferably 10 to 35 bar, more preferably 20 to 30 bar. If the continuous reaction is 2-step reaction, the first reaction and the second reaction can be carried out at pressure of 1 to 35 bar, or the first reaction can be carried out at pressure of 1 to 35 bar, preferably 10 to 35 bar, more preferably 20 to 30 bar and the second reaction can be carried out at pressure of the same as or slightly higher (for example, higher pressure of 0.5 bar) than the first reaction for effective feeding of unreacted excess alcohol gas from the second reactor into the first reactor. If metal catalyst is used in the continuous reaction, metal catalyst dissolved in alcohol can be continuously fed into the reactor with fatty acid.

Since the conventional esterification reaction of fatty acid using acid catalyst or solid acid catalyst is carried out at low temperature of less than 100° C. and water produced during the esterification reaction cannot be removed from the reaction system, the esterification reaction cannot be progressed beyond the reaction equilibrium. However, the esterification reaction of the present invention is performed at high temperature of 200 to 350° C. Thus, water produced during the esterification reaction can be continuously removed from the reaction system together with excess alcohol. Accordingly, the esterification reaction according to the present invention is progressed beyond the reaction equilibrium so that the conversion ratio of fatty acid is excellent near to the complete reaction. Specifically, in order to use the fatty acid alkyl ester as the bio-diesel, the total acid number (mg KOH/g) of the fatty acid alkyl ester should be less than a predetermined value. However, if the unreacted fatty acid component (carbon atom number of aliphatic part is 14 to 18) remains, the total acid number (mg KOH/g) of the produced fatty acid alkyl ester becomes high, and the fatty acid alkyl ester cannot satisfy the quality criteria for the bio-diesel. Since the unreacted fatty acid component have similar boiling point with fatty acid methyl ester, it is very difficult for the unreacted fatty acid component to be separated by the distillation. Thus, the unreacted fatty acid component should be removed by the complete esterification reaction. The method for preparing fatty acid alkyl ester according to the present invention has more than 99.7% of the conversion ratio of fatty acid into fatty acid alkyl ester, which satisfy the total acid number quality criteria for the bio-diesel. On the other hands, with the conventional method for preparing fatty acid alkyl ester using acid catalyst or solid acid catalyst such as ion exchange resin, it is difficult to increase the conversion ratio of fatty acid to be more than 99.7%. Also, in the method for producing fatty acid alkyl aster of the present invention, the acid catalyst used is not used, and the expensive production facilities durable to acid catalyst are unnecessary. Further, the rate of use of equipments for low or high pressure esterification reaction, such as equipments for preparing dimethylterephtalate, whose demand has been reduced all over the world, is decreasing. If these idle equipments are directly used for the present invention, fatty acid methyl ester suitable for bio-diesel can be economically made without specific conversion of an equipment to alter the designed pressure.

In the continuous process, alcohol is introduced by an amount of about 0.5 to 5 times by weight, preferably 0.5 to 3 times by weight, with respect to the introduced amount of fatty acid. Preferably, the metal catalyst is dissolved in the alcohol, and added to the reactor in the amount of 30 to 200 ppm (based on the metal component) by weight ratio with respect to fatty acid. The retention time of the total reaction process is 1 to 10 hours, preferably 3 to 5 hours. If the introduced amount of alcohol deviates from the above mentioned range, the reaction rate and the reaction yield can be reduced and it is economically undesirable.

The esterification reactor used in the present invention is a counter current column reactor operated at high pressure of 10 to 35 bar. The counter current column reactor used in the present invention has a number of trays which are installed horizontally to have a number of vertical compartments. One end of each tray is attached to inner wall of the esterification reactor and the other end of each tray is opened to have an opening part. The opening parts of the two adjoining trays are alternately installed with each other. Thus, through the opening part of the tray, the adjacent compartments communicate with each other and the reactants in the reactor pass through all the compartments sequentially (see FIG. 4). In the counter current column reactor, fatty acid fed through the upper part of the reactor and alcohol fed through the lower part of the reactor are subject to the esterification reaction at each tray in the condition of counter current while being transferred to other trays in order. Therefore, enough stay-length of reactants is guaranteed and short pass of reactants is prevented so that the first-in first-out effect is achieved. It is preferable that in each tray, a number of valves or bubble caps for the passage of alcohol gas are installed dispersedly in regular intervals in order for alcohol to be dispersedly supplied equally to reactants. The column reactor of the present invention adopts the counter current so that amount of water in the lower part of the reactor is maintained little. Therefore, even in the case of the reaction at high pressure (more than 10 bar), the same conversion efficiency can be obtained as in the case of the reaction at low pressure (less than 10 bar).

Figure 4:
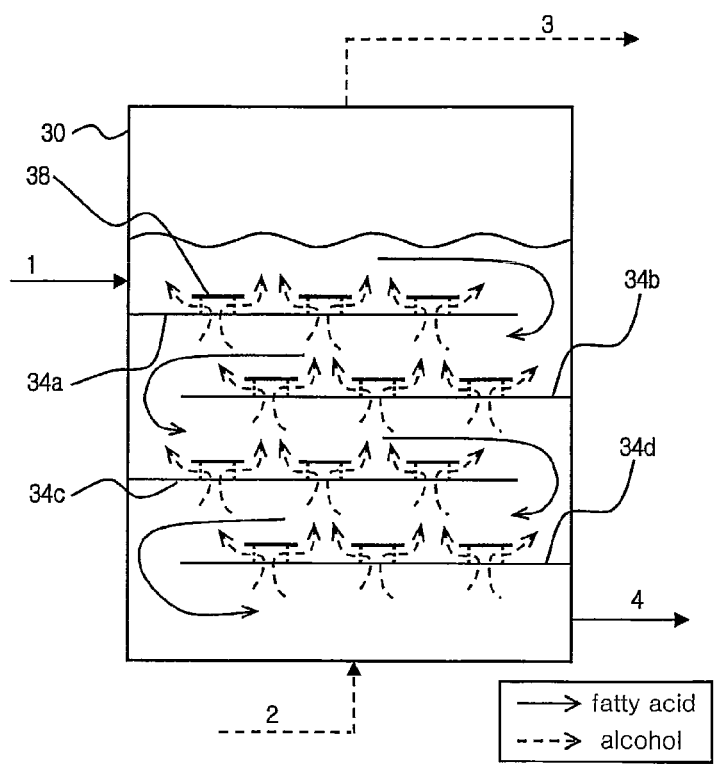
FIG. 4 is a drawing for showing an embodiment of the counter current column reactor for preparing fatty acid alkyl ester according to the present invention.

FIG. 4 is a drawing for showing an embodiment of the counter current column reactor useful for an apparatus for preparing fatty acid alkyl ester according to the present invention. The counter current column reactor of FIG. 4 is a full liquid type and has a counter current column reactor body 30 and a number of trays 34a, 34b, 34c, 34d where a number of valves 38 for the passage of gaseous alcohol or alcohol/water mixture are installed dispersedly in regular intervals. The trays 34a, 34b, 34c, 34d are horizontally installed inside the reactor body 30 to have a number of vertical compartments in the reactor body 30. One end of each tray 34a, 34b, 34c or 34d is opened to have an opening part by which the adjoining upper and lower compartments communicate with each other. The opening parts of the two adjoining trays are alternately installed with each other so that the reactants pass through all the compartments in order (the flow indicated by the solid line arrow in FIG. 4). Therefore, the counter current column reactor in FIG. 4 is full of liquid reactants. Moreover, valves 38 installed in the trays 34a, 34b, 34c, 34d are used for transferring gas to the upper side of the reactor. The number of the valve 38 is for example, 2 to 200, preferably 2 to 100, so as to equally disperse gas(alcohol) to reactants, and the number of the trays 34a, 34b, 34c, 34d is generally 2 to 100, preferably 2 to 50, though it may vary according to the design condition of the reactor. In the reactor, the counter current is used. Namely fatty acid 1 as raw material is fed into the top compartment of the upper part of the reactor 30 and then is transferred to lower compartments in order and alcohol 2 whose water content is low is fed into the bottom compartment of the lower part of the reactor 30 and then transferred to upper compartments in order. The alcohol 2 fed into the reactor 30 increases the conversion efficiency while passing each tray 34a, 34b, 34c, 34d through valves 38 in gaseous form. The mixture 3 of water generated from the reaction and unreacted excess alcohol is discharged as gas from the upper part of the reactor 30 and transferred to the alcohol recovery section 40 of FIG. 1. The high conversion rate can be obtained by using the one reactor mentioned above. However if the stay-length is not enough, the reaction can be carried out by increasing the number of tray of the reactor or by two-step reaction using two reactors as shown in FIG. 2 or 3.

Figure 5:
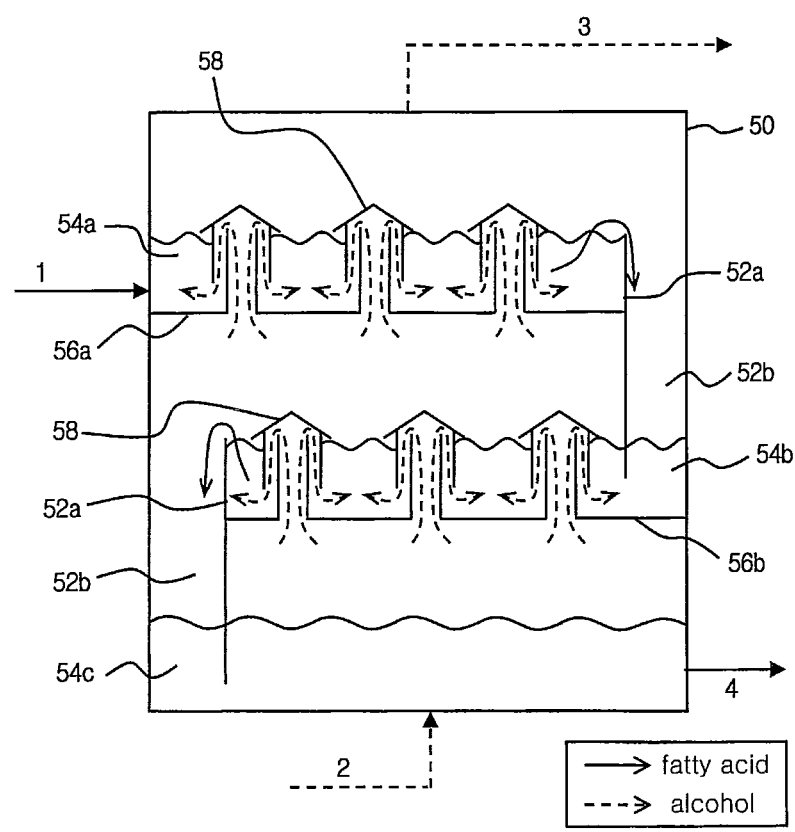
FIG. 5 is a drawing for showing another embodiment of the counter current column reactor for preparing fatty acid alkyl ester according to the present invention.

FIG. 5 is a drawing for showing another embodiment of the counter current column reactor useful for the present invention. The counter current column reactor shown in FIG. 5 comprises the reactor body 50 and a number of trays 56a, 56b inside the reactor body 50. The counter current column reactor is further equipped with bubble caps 58 and outlet weirs 52a to prevent unreacted fatty acid from short passing at each compartment of the reactor body 50 to the lower compartments and to more perfectly carry out the first-in first-out of reactants. The bubble cap 58 has its own outlet weirs therein to prevent gas and liquid from transferring to the lower part of the reactor and has a structure that gas flows through liquid in the upper tray when gas flows from the lower tray to the upper tray (dashed line arrow in FIG. 5). The outlet weir 52a is to transfer only liquid (reactants) stayed enough in each tray to the lower tray. The trays 56a, 56b divides the inside of the reactor 50 into a number of inner spaces, that is, compartments 54a, 54b and 54c. At one end of each tray 56a, 56b, is installed the outlet weir 52a whose top is opened. Through the outlet weir 52a is installed a downcomer 52b by which adjoining compartments communicate with each other. The outlet weirs 52a and the downcomers 52b of the adjoining trays are alternately installed so that reactants can pass through all the compartments 54a, 54b, 54c in order (the flow indicated by the solid line arrow in FIG. 5). The outlet weirs 52a divide the compartments 54a, 54b, 54c and the opening parts of the trays 56a and 56b in FIG. 5. Thus the opening parts of the trays 56a and 56b become the downcomer 52b. The level (height) of the top end of the outlet weir 52a should be determined for reactants to overflow the top end of the outlet weir 52a and flow to an adjoining lower tray only when reactants are stayed in each compartment 54a, 54b, 54c for a sufficient time and sufficient stay-length. Moreover, the level of the bottom end of the outlet weir 52a can be determined to be below the liquid level of reactants stayed in the lower compartment for the effective transfer of reactants. A number of bubble caps 58 are installed in regular intervals in the trays 56a, 56b for alcohol 2 to be dispersed in each compartments 54a, 54b, 54c equally. In the column current method using the reactor in FIG. 5, fatty acid 1 is fed into the upper part of the reactor and alcohol 2 whose water content is low is fed into the lower part, and alcohol 2 as gas phase passes through the bubble cap 58 to carry out esterification reaction in each tray 56a, 56b. The product 4 of the reaction comes out from the lower part of the reactor 50. The mixture 3 of water generated from the reaction and unreacted excess alcohol is discharged as gas phase from the upper part of the reactor 50 and transferred to the alcohol recovery section 40 of FIG. 1. At this moment, in each compartment 54a, 54b, 54c, the concentration of unreacted fatty acid 1 and the concentration of alcohol 2 are changed respectively. Fatty acid 1 is consumed by the esterification reaction as it goes to the lower compartments so that its concentration is lowered as it goes to the lower compartments. Alcohol 2 is mixed with water produced from the esterification reaction as it goes to the upper compartments so that its concentration is lowered as it goes to the upper compartments. Each compartment 54a, 54b, 54c and the outlet weir 52a prevent the short pass of unreacted fatty acid to the lower part of the reactor, and make a transfer route which provides enough stay-length and the first-in first-out passage, so that a high conversion efficiency can be obtained. The high conversion ratio can be obtained with the one reactor mentioned above. However, if the stay-length is not enough, the reaction can be carried out by increasing the number of tray of the reactor or by two-step reaction using two reactors as shown in FIG. 2 or 3.

Figure 6:
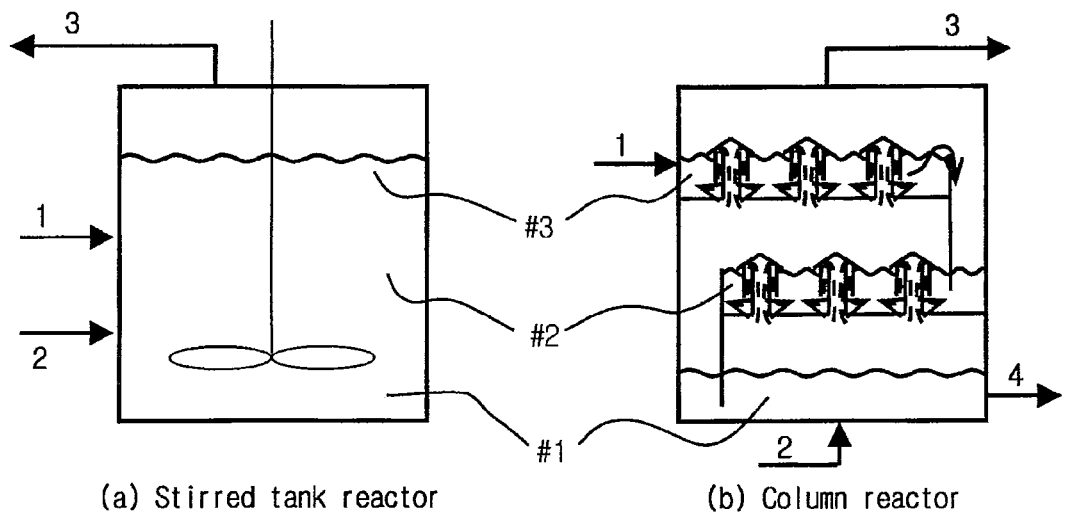
FIG. 6 is a drawing for showing the amount of water in each position inside the reactors, in carrying out esterification reaction of fatty acid and methanol using a high-pressure counter current column reactor of the present invention and a conventional low pressure stirred tank reactor equipped with a stirrer.
Figure 6:
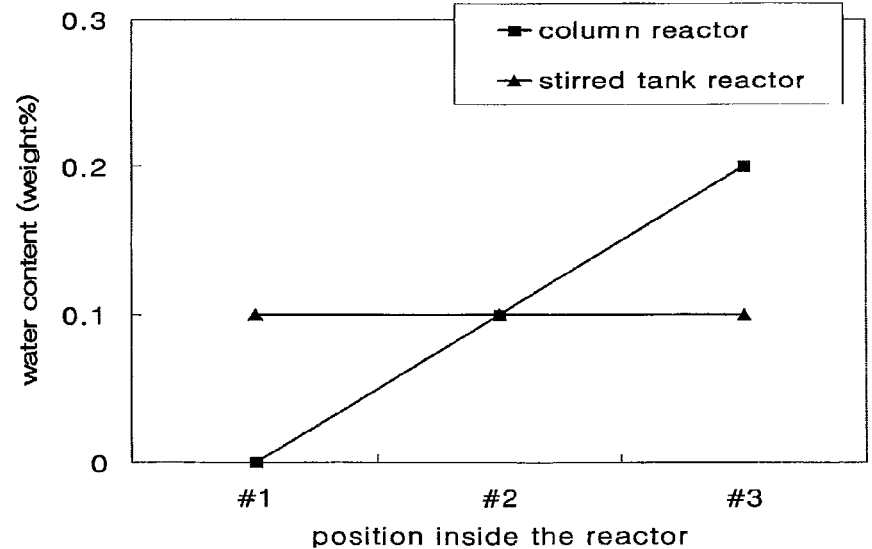

Hereinafter, referring to FIG. 6, the difference of the methods for preparing fatty acid alkyl ester between in the present invention and in the conventional techniques (Korean patent unexamined-publication No. 2007-106136 and International application publication No. WO 2007/126166) of the present applicant, is explained. FIG. 6 is a drawing for showing the amount of the water in each position inside the reactor, in case of carrying out the esterification reaction of fatty acid and methanol in the following Reaction 1 (R is an aliphatic group containing 14 to 24 of carbons) using the high pressure (over 10 bar) counter current column reactor of the present invention and the conventional low pressure (below 10 bar) stirred tank reactor equipped with a stirrer.

Reaction 1

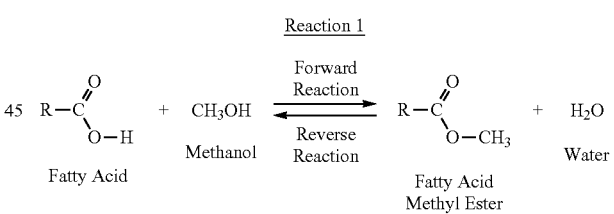

As shown in FIG. 6, in the stirred tank reactor equipped with a stirrer ((a) part), the concentration of water is same in all of the positions #1, #2, #3, and if the reactor is used for esterification reaction at low pressure (below 10 bar), water is removed easily so that the efficiency of conversion is excellent. However, if the reactor is used at high pressure (over 10 bar), concentration of water in the reactor increases because of the slow water removal, and the probability of an reverse reaction by which fatty acid alkyl ester is converted to fatty acid increases so that the efficiency of conversion is decreased. However, if the counter current column reactor ((b) part) divided by a number of trays is used for esterification reaction at high pressure (over 10 bar), the reaction even at high pressure of 10 to over 35 bar can be carried out with the same efficiency as the reaction at low pressure. As shown in FIG. 6, if the column reactor is used, fatty acid 1 is fed to the upper part of the reactor and alcohol 2 is fed into the lower part of the reactor, and alcohol/water mixture 3 provided by the reaction in each tray can not transfer to the lower tray but transfers only to the upper tray because of high reaction temperature. Therefore, water content in the upper part (#3 in FIG. 6) of the counter current reactor is high, but there is little water and much pure methanol in the lower part (#1 in FIG. 6) so that probability of reverse reaction is very low.

Figure 7:
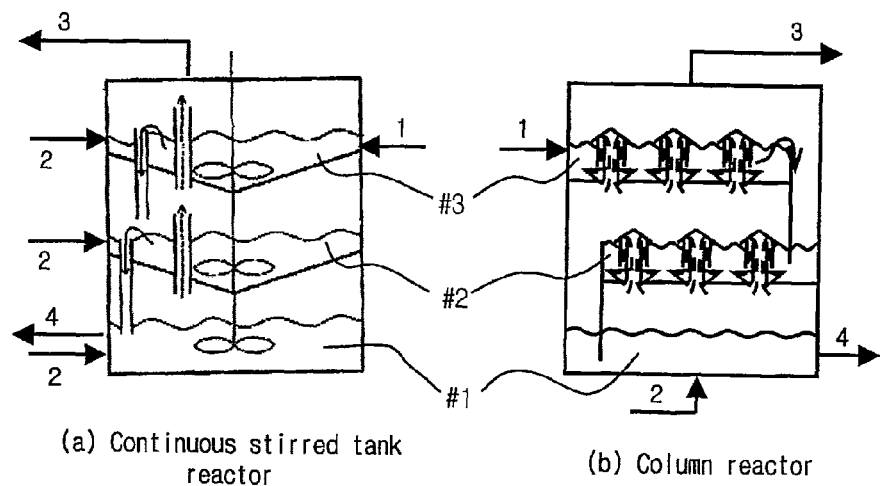
FIG. 7 is a drawing for showing the inflow amount of alcohol in each position inside the reactors, in case that the esterification reaction of fatty acid and methanol is carried out using a conventional continuous stirred tank reactor and the high pressure counter current column reactor of the present invention.
Figure 7:
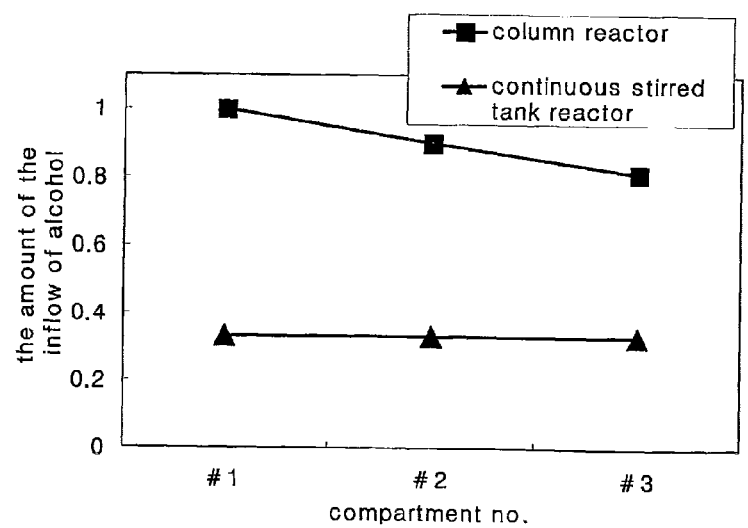

FIG. 7 is a drawing for showing the inflow amount of alcohol in each position inside the reactor, in the case that the esterification reaction of fatty acid and methanol is carried out using the continuous stirred tank reactor ((a) part) disclosed in Korean Patent unexamined-publication No. 2008-41438 and International application No. PCT/KR2008/1831 of the present inventor and the high pressure (over 10 bar) counter current column reactor of the present invention ((b) part). In the continuous stirred tank reactor shown in FIG. 7, the inside of the reactor is divided to a number of compartments by barriers, and alcohol is fed into each compartment and a stirrer is installed in each compartment. In FIG. 7, it is assumed that amount of fatty acid for the esterification reaction is 1, total methanol inflow for the reaction is 1, and 10% of methanol fed into each compartment can participate in the reaction. As shown in FIG. 7, if the continuous stirred tank reactor ((a) part) which has three compartments inside the reactor is used, the average amount of the inflow of alcohol fed into each compartment #1, #2, #3 is 0.33. However, if the column reactor ((b) part) is used, total alcohol of 1 is fed into the lower tray #1, and alcohol of 0.9 which remains after methanol of 0.1 has been used for the reaction at the lower tray #1, transfers to the upper tray #2 due to the high temperature. In the tray #2 where methanol of 0.9 has been fed, alcohol of 0.09 is used, and alcohol of 0.81 is discharged to the upper tray #3. Therefore, as shown in FIG. 7, if the column reactor is used, relatively much alcohol is fed in all of the position in the reactor so that the forward reaction of esterification can be promoted and efficiency of the reaction can be raised. Moreover, if the column reactor is used, each tray prevents unreacted fatty acid from short passing and guarantees enough stay-length, and the first-in first-out effect is achieved to increase the conversion efficiency. By these advantages, the optimum condition of reaction for preparing fatty acid methyl ester of low acid value is achieved. Moreover, the column reactor in the present invention is economically favorable because valves or bubble caps are used instead of agitator that electric power is consumed.

Figure 8:
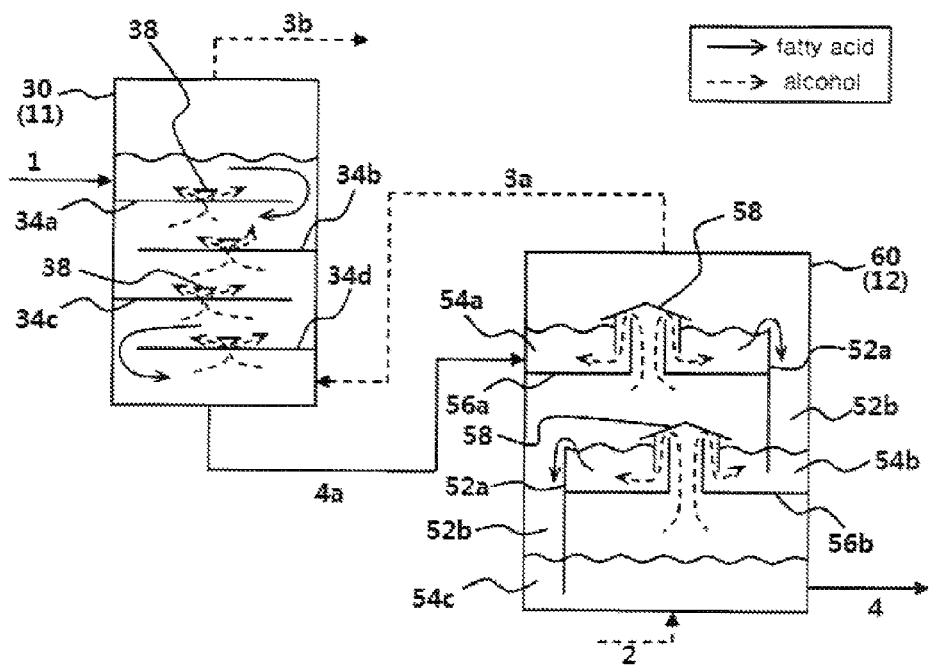
FIGS. 8 to 11 are drawings for showing embodiments of the connection structures of column reactors useful for the apparatus of the present invention.
Figure 9:
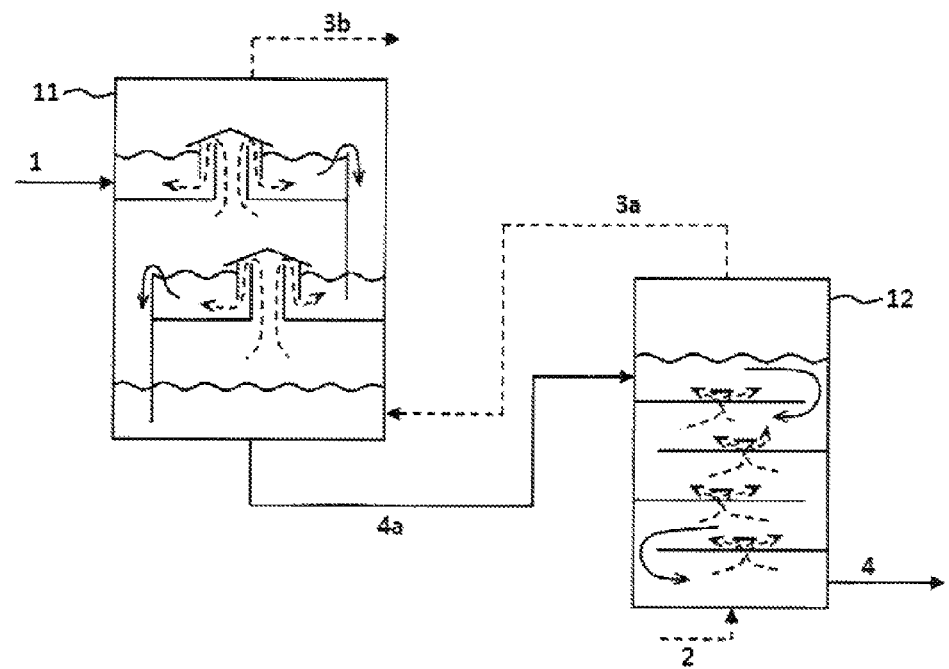
Figure 10:
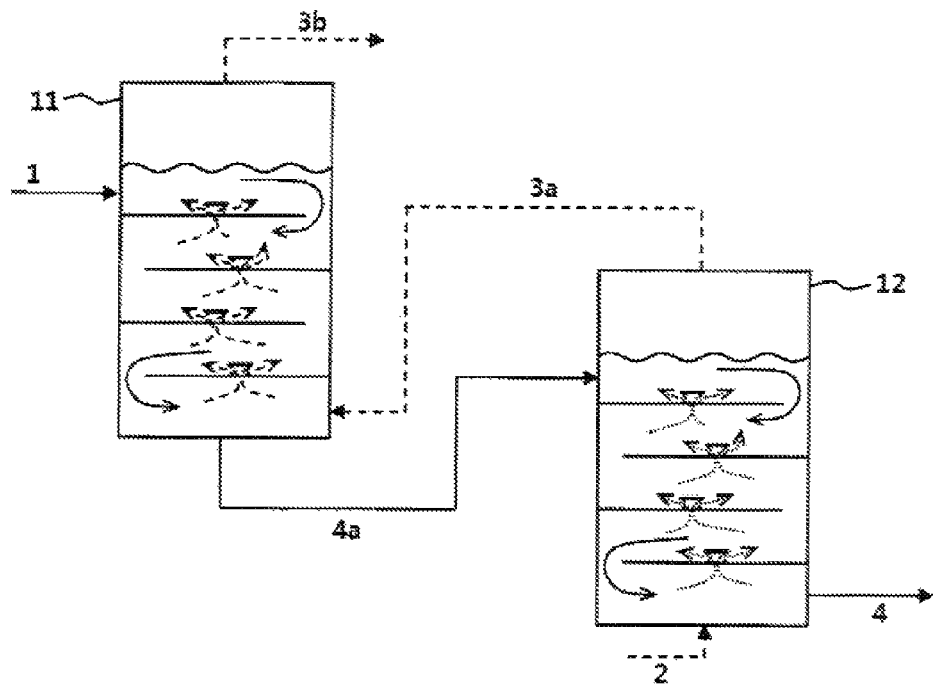
Figure 11:
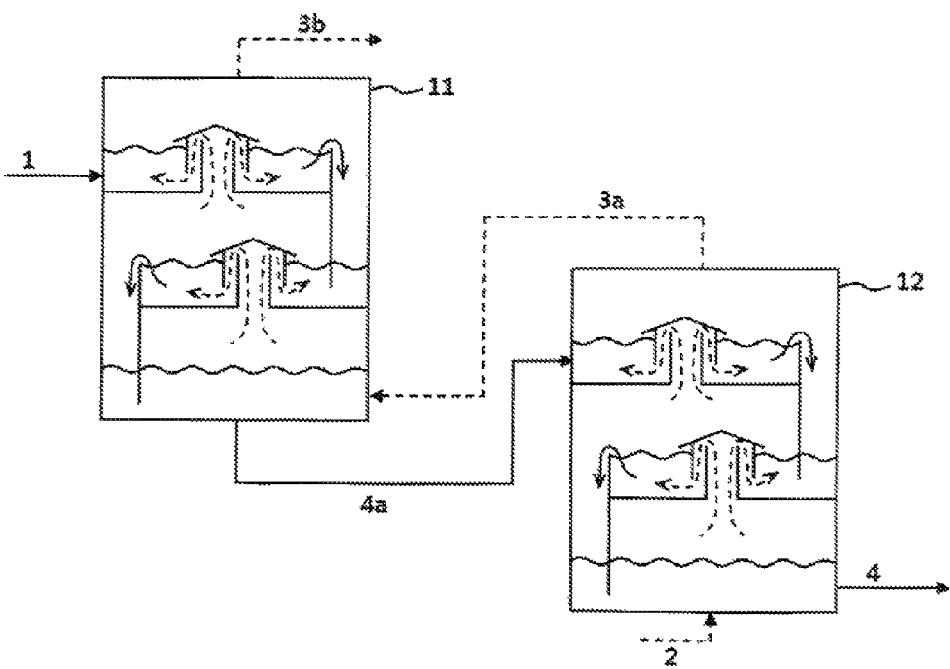

FIGS. 8 to 11 are drawings for showing an embodiment of the connection structure of column reactors useful for the present invention. The connection structure is for ensuring the enough stay-length by connecting two reactors as shown in FIG. 2 or 3, if the stay-length is not enough with one reactor. FIG. 8 shows an embodiment of connecting the full liquid type counter current column reactor in FIG. 4 and the counter current column reactor equipped with the outlet weir in FIG. 5. The column reactor in FIG. 8 comprises the first reactor 30(11) where some (for example, 80 to 95%) of the total fatty acid is converted to fatty acid alkyl ester and the second reactor 50(12) where the remaining fatty acid from the first reactor is converted to fatty acid alkyl ester. As the product of the first reaction, crude fatty acid alkyl ester 4a that the reaction is not finished, is fed into the upper part of the second reactor 50 from the lower part of the first reactor 30(11), 11, and alcohol 2 with low water content is fed into the lower part of the second reactor 50(12) and esterification reaction is carried out. The crude fatty acid alkyl ester 4, the product of the second reaction is discharged from the lower part of the second reactor 50(12) and is transferred to the refining section 20 in FIG. 1. The mixture 3a of water generated from the second reaction and unreacted excess alcohol is discharged as gas from the upper part of the second reactor 50 and fed into the lower part of the first reactor 30(11) to carry out esterification reaction with fatty acid 1, and the mixture 3b of water generated from this reaction and unreacted excess alcohol is discharged as gas from the upper part of the first reactor 30(11). FIG. 9 is a drawing for showing an embodiment of connecting the counter current column reactor equipped with the outlet weir in FIG. 5 as the first reactor 11 and the full liquid type counter current column reactor in FIG. 4 as the second reactor 12. FIG. 10 is a drawing for showing an embodiment of connecting the full liquid type counter current column reactor in FIG. 4 as the first reactor 11 and the second reactor 12. FIG. 11 is a drawing for showing an embodiment of connecting the counter current column reactor equipped with the outlet weir in FIG. 5 as the first reactor 11 and the second reactor 12.

As mentioned above, by connecting same or different two or more reactors in succession, most of total fatty acid is converted to fatty acid alkyl ester in the first reactor 11 and the remaining fatty acid is converted in the second reactor 12, and the efficiency of conversion can be increased. Moreover, by transferring fatty acid and alcohol after esterification reaction at the condition of counter current to other trays in order, short pass of unreacted fatty acid is prevented and enough stay-length thereof is guaranteed, and the first-in first-out effect is achieved to raise the efficiency of conversion of fatty acid to fatty acid alkyl ester. Therefore, by the method and apparatus for preparing fatty acid alkyl ester according to the present invention, high quality fatty acid alkyl ester can be made not only at low pressure but also at high pressure of 10 to 35 bar, and various esterification reactors such as conventional reactor for preparing DMT (dimethylterephtalate) can be used without additional modification.

Most of the crude fatty acid alkyl ester 4 obtained by esterification reaction of the present invention is fatty acid alkyl ester. However, in order to use the fatty acid alkyl ester of the present invention as the industrial fuel or bio-diesel fuel, low molecular weight fatty acid alkyl esters, high molecular weight fatty acid alkyl esters, residues, and so on should be removed from the crude fatty acid alkyl ester 4. Especially in the case of fatty acid methyl ester, fatty acid alkyl ester having carbon atom number of aliphatic part being less than 14 or more than 24 and other low molecular weight impurities should be removed, so as to satisfy the quality criteria of the bio-diesel. Therefore, in the present invention, the crude fatty acid alkyl ester 4 is refined by the two-step distillation process. Referring to FIG. 1, in the first refining section 20 of the present invention, 1 to 10 weight %, preferably 2 to 5 weight % of an introduced amount (feed) is removed through the upper part of a distillation column by maintaining the temperature of the lower part of the distillation column to be 150 to 250° C., preferably 180 to 220° C. at the vacuum of 0.1 to 150 torr, preferably 0.1 to 40 torr. When the amount removed through the upper part of the distillation column is less than 1 weight % of the feed, impurities having low boiling point cannot be sufficiently removed. When the amount removed through the upper part of the distillation column is more than 10 weight % of the feed, the yield may be reduced. In this case, most of the impurities having low boiling point which are removed through the upper part of the distillation column are low molecular weight fatty acid alkyl ester. Thus, the removed impurities can be directly used as a fuel for boilers, etc, without additional process. In the second refining section 30 of the present invention, the impurities of 1 to 25 weight % of an introduced feed are left for removal in the lower part of the distillation column, and the refined fatty acid alkyl ester of high purity is extracted through the upper part of the distillation column by maintaining the temperature of the lower part of the distillation column to be 200 to 300° C., preferably 220 to 280° C. at the vacuum of 0.1 to 150 torr, preferably 0.1 to 40 torr. The amount of the removed impurities (residue) in the second refining section can be varied according to the composition of the fatty acid raw material. However, when the amount remaining on the lower part of the distillation column is less than 1 weight % of the feed, the purity of fatty acid alkyl ester can be deteriorated. When the amount remaining on the lower part of the distillation column is more than 25 weight % of the feed, the yield may be reduced. Here, most of the remaining impurities are fatty acid alkyl ester having carbon atom number of aliphatic part being more than 24. Thus, the remaining impurities can be used as fuel for boilers, etc. Besides, the metal catalyst used in reaction is extracted with the residue and does not deteriorate the quality of fatty acid alkyl ester. Then, the metal catalyst extracted with residue may be discarded or may be reused by recycling after combustion. The fatty acid alkyl ester refined by the above mentioned method, specifically fatty acid methyl ester satisfies all quality criteria on the bio-diesel in Korea and foreign countries including U.S.A. and Europe. Therefore, the fatty acid alkyl ester of the present invention can be directly used as the bio-diesel.

On the other hand, water produced during the esterification reaction of the present invention is extracted from the reaction section 10 together with excess alcohol which is unreacted in the esterification reaction, and the mixture of water and alcohol is separated at the alcohol recovery section 40. After the separation, water is transferred to the waste water disposal plant, and the alcohol is recycled to the reaction section 10 for reuse. The alcohol recovery section 40 includes a distillation column and affiliated facilities therefor. The temperature of the lower part of the distillation column of the alcohol recovery section 40 is controlled according to the boiling point of alcohol so as to distil alcohol. The distilled and reused alcohol can contain 0 to 10 weight %, specifically 0.001 to 10 weight % of water. If the amount of water contained in alcohol is more than 10 weight %, the esterification rate in the reaction section 10 may be reduced. Also, in case of using methanol, by using only single distillation column, methanol can be refined with sufficiently high purity and can be recycled to the reaction section 10. In case of using alcohol having at least 2 carbon atoms, for example, ethanol, the alcohol/water azeotrope is extracted from the distillation column of the alcohol recovery section 40, and is subject to dehydration process to remove water. Then the water removed alcohol is recycled to the reaction section 10.

Hereinafter, the preferable examples are provided for better understanding of the present invention. However, the present invention is not limited to the following examples.

Comparative Example 1

Preparation of Fatty Acid Methyl Ester (Batch Process)

The esterification reaction was carried out by one-step reaction using the batch type continuous stirred tank reactor (CSTR) shown in (a) of FIG. 6. Firstly, 1 kg of fatty acid distillate and 0.5 kg of methanol in which 0.8 g of tetrabutyl titanate was dissolved were introduced into the reactor. The reactor was controlled to temperature of 300° C. and pressure of 30 bar, and 1300 g of methanol was further added to the reactor, and the reaction was carried out for 4 hours. The conversion ratio for fatty acid methyl ester by the above mentioned method was 99.8%. The final total acid number was 0.34 mg KOH/g.

Comparative Example 2

Preparation of Fatty Acid Methyl Ester (Batch Process)

The esterification reaction was carried out by one-step reaction using the batch type CSTR shown in (a) of FIG. 6. Firstly, 1 kg of fatty acid distillate and 0.5 kg of methanol in which 0.8 g of tetrabutyl titanate was dissolved were introduced into the reactor. The reactor was controlled to temperature of 300° C. and pressure of 20 bar, and 975 g of methanol was further added to the reactor, and the reaction was carried out for 3 hours. The conversion ratio for fatty acid methyl ester by the above mentioned method was 99.8%. The final total acid number was 0.36 mg KOH/g.

Comparative Example 3

Preparation of Fatty Acid Methyl Ester (Batch Process)

The esterification reaction was carried out by one-step reaction using the batch type CSTR shown in (a) of FIG. 6. Firstly, 1 kg of fatty acid distillate and 0.5 kg of methanol in which 0.8 g of tetrabutyl titanate was dissolved were introduced into the reactor. The reactor was controlled to temperature of 300° C. and pressure of 10 bar, and 650 g of methanol was further added to the reactor, and the reaction was carried out for 2 hours. The conversion ratio for fatty acid methyl ester by the above mentioned method was 99.8%. The final total acid number was 0.34 mg KOH/g.

Comparative Example 4

Preparation of Fatty Acid Methyl Ester (Continuous Process)

The esterification reaction was carried out by one-step reaction using the continuous stirred tank reactor (CSTR) shown in (a) of FIG. 7. Firstly, the reactor was controlled to temperature of 300° C. and pressure of 20 bar. As feeding fatty acid distillate, which had been obtained from distillation of crude palm oil, by a flow of 6 g/min, a little methanol in which 50 ppm of cobalt acetate had been dissolved in proportion to an input of fatty acid distillate was fed simultaneously into the upper part of the reactor, and 99.7% pure methanol 2 was fed by a flow of 6 g/min into the reactor to react during guaranteed 3-hour stay-length. After the finish of the reaction, the conversion ratio for fatty acid methyl ester by the above mentioned method was 99.5%. The final total acid number was 0.87 mg KOH/g. The fatty acid methyl ester obtained from this comparative example 4 was not suitable for the quality standard of fatty acid methyl ester for the bio-diesel used for vehicle fuel which needs 0.5 mg KOH/g of total acid value.

Comparative Example 5

Preparation of Fatty Acid Methyl Ester (Continuous Process)

The esterification reaction was carried out by one-step reaction using the continuous stirred tank reactor (CSTR)

shown in (a) of FIG. 7. Firstly, the reactor was controlled to temperature of 300° C. and pressure of 10 bar. As feeding fatty acid distillate, which had been obtained from distillation of crude palm oil, by a flow of 6 g/min, a little methanol in which 50 ppm of cobalt acetate had been dissolved in proportion to an input of fatty acid distillate was fed simultaneously into the upper part of the reactor, and 99.7% pure methanol 2 was fed by a flow of 6 g/min into the reactor to react during guaranteed 3-hour stay-length. After the finish of the reaction, the conversion ratio for fatty acid methyl ester by the above mentioned method was 99.7%. The final total acid number was 0.5 mg KOH/g.

Comparative Example 6

Preparation of Fatty Acid Methyl Ester (Continuous Process)

The esterification reaction was carried out by one-step reaction using the continuous stirred tank reactor (CSTR) shown in (a) of FIG. 7. Firstly, the reactor was controlled to temperature of 300° C. and pressure of 5 bar. As feeding fatty acid distillate, which had been obtained from distillation of crude palm oil, by a flow of 6 g/min, a little methanol in which 50 ppm of cobalt acetate had been dissolved in proportion to an input of fatty acid distillate was fed simultaneously into the upper part of the reactor, and 99.7% pure methanol 2 was fed by a flow of 6 g/min into the reactor to react during guaranteed 3-hour stay-length. After the finish of the reaction, the conversion ratio for fatty acid methyl ester by the above mentioned method was 99.7%. The final total acid number was 0.42 mg KOH/g.

Example 1

Preparation of Fatty Acid Methyl Ester (Continuous Process)

The esterification reaction was carried out by two-step reaction using the reactors shown in FIG. 11. Firstly, the first reactor 11 was controlled to temperature of 300° C. and pressure of 20 bar. As feeding fatty acid distillate by a flow of 10 g/min, a little methanol in which 50 ppm of cobalt acetate (with respect to fatty acid distillate) had been dissolved in proportion to an input of fatty acid distillate was fed simultaneously into the upper part of the first reactor 11, and gaseous methanol/water mixture from the second reactor 12 was fed directly into the lower part of the first reactor 11 to react during guaranteed 1.5-hour stay-length. As feeding the product 4a of the above mentioned first reaction into the upper part of the second reactor 12, 99.7% pure methanol 2 was fed by a flow of 10 g/min into the lower part of the second reactor 12. Wherein the second reactor 12 was controlled to temperature of 300° C. and pressure of 20.5 bar, and the residence time of the reactants (reaction time) was 1.5 hours. After the finish of the reaction, the conversion ratio for fatty acid methyl ester 4 from the lower part of the second reactor 12 was 99.8% (total acid number: less than 0.4 mg KOH/g).

Example 2

Preparation of Fatty Acid Methyl Ester (Continuous Process)

The esterification reaction was carried out by two-step reaction using the reactors shown in FIG. 11. Firstly, the first reactor 11 was controlled to temperature of 300° C. and pressure of 10 bar. As feeding fatty acid distillate by a flow of 10 g/min, a little methanol in which 50 ppm of cobalt acetate (with respect to fatty acid distillate) had been dissolved in proportion to an input of fatty acid distillate was fed simultaneously into the upper part of the first reactor 11, and gaseous methanol/water mixture from the second reactor 12 was fed directly into the lower part of the first reactor 11 to react during guaranteed 1.5-hour stay-length. As feeding the product 4a of the above mentioned first reaction into the upper part of the second reactor 12, 99.7% pure methanol 2 was fed by a flow of 10 g/min into the lower part of the second reactor 12. Wherein the second reactor 12 was controlled to temperature of 300° C. and pressure of 10.5 bar, and the residence time of the reactants (reaction time) was 1.5 hours. After the finish of the reaction, the conversion ratio for fatty acid methyl ester 4 from the lower part of the second reactor 12 was 99.8% (total acid number: less than 0.4 mg KOH/g).

Example 3

Preparation of Fatty Acid Methyl Ester (Continuous Process)

The esterification reaction was carried out by two-step reaction using the reactors shown in FIG. 11. Firstly, the first reactor 11 was controlled to temperature of 300° C. and pressure of 5 bar. As feeding fatty acid distillate by a flow of 10 g/min, a little methanol in which 50 ppm of cobalt acetate (with respect to fatty acid distillate) had been dissolved in proportion to an input of fatty acid distillate was fed simultaneously into the upper part of the first reactor 11, and gaseous methanol/water mixture from the second reactor 12 was fed directly into the lower part of the first reactor 11 to react during guaranteed 1.5-hour stay-length. As feeding the product 4a of the above mentioned first reaction into the upper part of the second reactor 12, 99.7% pure methanol 2 was fed by a flow of 10 g/min into the lower part of the second reactor 12. Wherein the second reactor 12 was controlled to temperature of 300° C. and pressure of 5.5 bar, and the residence time of the reactants (reaction time) was 1.5 hours. After the finish of the reaction, the conversion ratio for fatty acid methyl ester 4 from the lower part of the second reactor 12 was 99.8% (total acid number: less than 0.4 mg KOH/g).

The experiment conditions and results of Comparative Examples 1 to 6 and Examples 1 to 3 are set forth in the following Table 1.

TABLE 1

|  | Example 1 | Example 2 | Example 3 | Comparative Example 1 | Comparative Example 2 | Comparative Example 3 | Comparative Example 4 | Comparative Example 5 | Comparative Example 6 |
|---|---|---|---|---|---|---|---|---|---|
| reactor | counter current continuous type | counter current continuous type | counter current continuous type | CSTR batch type | CSTR batch type | CSTR batch type | CSTR continuous type | CSTR continuous type | CSTR continuous type |

TABLE 1-continued

|  | Example 1 | Example 2 | Example 3 | Comparative Example 1 | Comparative Example 2 | Comparative Example 3 | Comparative Example 4 | Comparative Example 5 | Comparative Example 6 |
| --- | --- | --- | --- | --- | --- | --- | --- | --- | --- |
| pressure (bar) | 20 | 10 | 5 | 30 | 20 | 10 | 20 | 10 | 5 |
| temperature (° C.) | 300 | 300 | 300 | 300 | 300 | 300 | 300 | 300 | 300 |
| reaction time (hr) | 1.5/1.5 (3) | 1.5/1.5 (3) | 1.5/1.5 (3) | 4 | 3 | 2 | 3 | 3 | 3 |
| conversion ratio (%) | 99.8 | 99.8 | 99.8 | 99.8 | 99.8 | 99.8 | 99.5 | 99.7 | 99.7 |
| total acid number (mgKOH/g) | less than 0.4 | less than 0.4 | less than 0.4 | 0.34 | 0.36 | 0.34 | 0.87 | 0.5 | 0.42 |

As shown in Table 1, the method for preparing fatty acid alkyl ester according to the present invention achieves high reaction rate and conversion ratio at low and high pressure, especially at high pressure.

The invention claimed is:

1. A method for preparing fatty acid alkyl ester for bio-diesel fuel comprising the step of carrying out a counter current type esterification reaction of fatty acid and alcohol in each tray of a counter current column reactor at a temperature of 200 to 350° C. and a pressure of 10 to 35 bar,
   wherein a raw material of the fatty acid is fed to an upper part of the counter current column reactor and alcohol is fed to a lower part of the counter current column reactor;
   wherein the counter current column reactor has a number of trays which are installed horizontally to have a number of vertical compartments;
   wherein each of a number of trays has an opening part at one end thereof to communicate one compartment with an adjoining compartment;
   wherein the opening parts of two adjoining trays are alternately installed with each other: and
   wherein the raw material of fatty acid is fed to a top compartment at the upper part of the counter current column reactor and then is transferred to lower compartments in order, and the alcohol is fed to a bottom compartment at the lower part of the counter current column reactor and then is transferred to upper compartments in order.

2. The method for preparing fatty acid alkyl ester for bio-diesel fuel of claim 1, wherein a number of valves or bubble caps for a passage of alcohol gas are installed dispersedly in regular intervals in each tray.

3. The method for preparing fatty acid alkyl ester for bio-diesel fuel of claim 1, wherein the mixture of water generated from the esterification reaction and unreacted excess alcohol is discharged as gas phase from the upper part of the counter current column reactor.

4. The method for preparing fatty acid alkyl ester for bio-diesel fuel of claim 1, wherein, in one end of each tray an outlet weir whose top is opened and which divides the compartment and the opening part of the tray is vertically installed, and when reactants are fed, the reactants overflow from the top of the outlet weir and transfer to an adjoining lower tray.

5. The method for preparing fatty acid alkyl ester for bio-diesel fuel of claim 1, wherein the counter current column reactor includes a first reactor where part of fatty acid is converted to fatty acid alkyl ester and a second reactor where a remaining fatty acid from the first reactor is converted to fatty acid alkyl ester, the first reactor and second reactor being connected to each other.

6. The method for preparing fatty acid alkyl ester for bio-diesel fuel of claim 5, wherein crude fatty acid alkyl ester, a product of a first esterification reaction at the first reactor, is fed into a upper part of the second reactor and the alcohol is fed into a lower part of the second reactor so that a second esterification reaction is carried out in the second reactor;
   fatty acid alkyl ester, a product of the second esterification reaction is discharged from the lower part of the second reactor; and
   a mixture of water generated from the second esterification reaction and unreacted excess alcohol is discharged as gas phase from the upper part of the second reactor and then fed into the lower part of the first reactor, to carry out the first esterification reaction with the fatty acid.

7. The method for preparing fatty acid alkyl ester for bio-diesel fuel of claim 1, wherein, the pressure is 20 to 30 bar.

8. An apparatus for preparing fatty acid alkyl ester for bio-diesel fuel comprising:
   a columnar reactor body; and
   a number of trays which are installed horizontally to have a number of vertical compartments in the columnar reactor body and have gas valves dispersedly installed in regular intervals,
   wherein each of the number of trays has an opening part at one end thereof to communicate one compartment with an adjoining compartment;
   the opening parts of two adjoining trays are alternately installed with each other; and a raw material of fatty acid is fed to an upper pan of the columnar reactor body and alcohol is fed to a lower part of the columnar reactor body to carry out counter current type esterification reaction in each tray of the columnar reactor at a temperature of 200 to 350° C. and pressure of 10 to 35 bar; and
   wherein the raw material of fatty acid is fed to a top compartment at the upper part of the columnar reactor body and then is transferred to lower compartments in order, and the alcohol is fed to a bottom compartment at the lower part of the columnar reactor body and then is transferred to upper compartments in order.

* * * * *